United States Patent [19]

Ethridge

[11] Patent Number: 4,725,234

[45] Date of Patent: Feb. 16, 1988

[54] ALVEOLAR BONE GRAFTING PROCESS WITH CONTROLLED SURFACE ACTIVE CERAMICS

[76] Inventor: Edwin C. Ethridge, 1404 Monte Sano Blvd., SE., Huntsville, Ala. 35801

[21] Appl. No.: 766,050

[22] Filed: Aug. 15, 1985

[51] Int. Cl.$^4$ .............................................. A61C 5/00
[52] U.S. Cl. .................................. 433/215; 128/92 YQ
[58] Field of Search ............ 128/92 YQ, 92 YR, 92 R; 433/215

[56] References Cited

U.S. PATENT DOCUMENTS

| | | | |
|---|---|---|---|
| 4,024,639 | 5/1977 | Weiss et al. | 433/173 |
| 4,308,064 | 12/1981 | Takami et al. | 128/92 YQ |
| 4,356,572 | 11/1982 | Guillemin et al. | 128/92 YQ |
| 4,472,840 | 9/1984 | Jefferies | 128/92 YQ |
| 4,497,075 | 2/1985 | Niwa et al. | 623/16 |
| 4,548,959 | 10/1985 | Nagai et al. | 623/16 |
| 4,599,085 | 7/1986 | Reiss et al. | 623/16 |
| 4,629,464 | 12/1986 | Takama et al. | 623/16 |

*Primary Examiner*—Robert Peshock
*Attorney, Agent, or Firm*—George J. Porter

[57] ABSTRACT

Materials and dental procedures are disclosed for the treatment of resorbed or diseased periodontal and alveolar bone tissues. Biocompatible nonresorbable ceramic mixtures and compounds containing silicon, calcium, phosphorous, and sodium oxides and flurides are prepared as powders or spheres and applied to defects or areas where it is desired to recontour the bone structure. This technique permits an improved method for corrective peridontal procedures and for alveolar ridge augmentation.

30 Claims, 6 Drawing Figures

ALVEOLAR BONE GRAFTING PROCESS WITH CONTROLLED SURFACE ACTIVE CERAMICS

FIELD OF THE INVENTION

This invention relates to a method of treatment of diseased bone tissues. More specifically, the invention relates to materials and medical and dental treatment of diseased periodontal and alveolar bone tissues, including a method for corrective periodontal procedures and for alveolar ridge augmentation.

BACKGROUND OF THE INVENTION

Periodontal disease is a chronic infection of the periodontal ligament of teeth which plagues a major portion of the general population. Plaque accumulation triggers inflammation of the marginal gingiva. If the inflammation is permitted to persist, the gingivitis can worsen to become periodontitis. As a response to the presence of bacteria, lytic enzymes such as collagenase accumulate at the site. This inflammatory process causes destruction of the collagen matrix and the inserted gingival fiber apparatus. Repeated infection and neglect result in the periodontal ligament being slowly destroyed. With the destruction of the periodontal ligament follows the resorption of bone surrounding the affected teeth. With continued infection of the periodontal ligament, ligament destruction, and bone resorption, little viable bone tissue remains to support the tooth. The overall result is the formation of a pocket around the tooth. This progressive disease ultimately leads to the loss of the affected tooth unless treatment is obtained. No current treatment is effective in regenerating the lost bone around the tooth. As a result, the permanent bone defect is a haven for plaque and bacteria that cause periodontal disease so that recurrence is common.

There are many technical approaches to periodontal therapy but the infrabony defect remains the Nemesis for the periodontist. Recently there has been an escalated effort in the direction of regenerative periodontal therapy with the ultimate goal of stimulating bone growth, regeneration of a functional periodontium at the site of the pocket, and the reattachment of epidermal and connective tissues. Successful therapy will require a larger degree of predictability and reproducibility than is currently available. The unpredictability of bone and periodontum regeneration is the limiting factor in regenerative therapy.

Autogenous bone transplants are commonly used for regenerative therapy since some new bone regeneration is frequently observed. The disadvantage is that a second surgical procedure is required to obtain the transplant material. This requires more time, expense to the patient, a more complicated procedure, and the final results are less than desired. Allografts are more advantageous since an unlimited amount of material is available and a second operation is not required. Demineralized allogenic bone matrix (DABM) is another natural biomaterial being used clinically for osseous reconstruction. In general, all bone grafts, regardless of the type, elicit the same type of repair response and are of limited success (Barrington, 1981; Stahl, 1977; Haggerty, 1977; Urist, 1965).

It is very desirable to have man-made materials that can be used in place of tissue grafts. There are no problems with immune response, the material can be readily prepared and can have a very long shelf life. Unfortunately, most biomedical engineering materials do not enhance bone formation and have a history of limited success.

A number of materials containing biocompatible calcium phosphate have been developed. The first of these contain primarily calcium and phosphrous compounds. Search of the prior art reveals the following calcium-phosphate based biocompatible implant materials disclosed in the following patents:

Driskell, Heller and Koenigs (U.S. Pat. No. 3,913,229 issued Oct. 21, 1975) disclosed dental methods and materials for use in treating diseased or traumatized teeth and periodontal tissues and is especially suitable for endodontic (pulp caping, root canal, and tooth replanting techniques) treatments of teeth. The materials utilized are the physiologically compatible and soluble calcium phosphate compounds, whitlockite and brushite. These materials consist entirely of calcium phosphate compounds. The material is prepared into a porous agregate paste or powder and positioned adjacent to the calcified tissue. The particles are a small size such that the putty like mixture exhibits colloidal properties.

Niwa et. al. (U.S. Pat. No. 4,497,075 issued Feb. 5, 1985) disclose a material for filling defects or hollow portions of bone tissues. The material is a crystalline calcium phosphate apatite compound with the calcium to phosphate ratio in the range of 1.33 to 1.95.

Jarcho (U.S. Pat. No. 4,097,935 issued July 4, 1978) discloses a new process for manufacturing polycrystalline ceramics of pure hydroxylapatite and a material consisting of a mixture of hydroxylapatite and whitlockite with molar ratios of calcium to phosphorus in the ranges of 1.57 to 1.67. The material is to be used as a filter in dental cements and as a dental and surgical prosthetic material. Jarcho (U.S. Pat. No. 4,207,306 issued June 10, 1980) also discloses a process for producing polycrystalline ceramic oxides.

Ebihara et. al. (U.S. Pat. No. 4,113,500 issued Sept. 12, 1978) disclose a process for forming by molding and sintering a hydroxylapatite powder also containing magnesium. The object has high mechanical strength and is reported to be biocompatible. It is proposed to be suitable for a medical implant materials such as prosthetic teeth or bones.

Guillemin et. al. (U.S. Pat. No. 4,356,572 issued Nov. 2, 1982) disclosed a biodegradable bone implant composed of resorbable calcium carbonate. The implant is to be used an the form of a filler or replacement part for bone.

Takami and Kondo (U.S. Pat. No. 4,308,064 issued Dec. 29, 1981 and U.S. Pat. No. 4,376,168 issued Mar. 8, 1983) disclose a calcium phosphate ceramic containing yittrium oxide which improves the mechanical properties. It is considered a strong and biocompatible material.

In the alveolar bone environment around teeth implants, these types of materials (including tricalcium phosphate and hydroxylapatite) do not produce the extent of bone regeneration that is desirable. The ultimate result is similar to that with bone implants. The results remain far from the desired correction of the periodontal pocket. This may be partially due to the fact that this material does not bond to bone by the same mechanism as the surface active ceramic used with the current process.

Controlled surface active ceramics have been developed over the past decade and are known to the art. These materials consist of four primary constituents with the general composition 40 to 60 weight percent silicon dioxide, 10 to 35 weight percent sodium oxide, 15 to 45 weight percent calcium oxide, and 6 weight percent phosporus pentoxide. This general composition range is represented by FIG. 1. Two of the primary ingredients are calcium oxide and phosporus pentoxide. These are selected in proportions such that the Ca/P ratio is similar to that for hydroxyapatite bone mineral. Sodium ions are added to the composition in the form of sodium oxide in order to flux the molten glass batch, aid glass formation, and stabilize the local aqueous environment of the surrounding tissues. These three constituents are held in glassy form by silicon dioxide which serves as a network former decreasing the solubility rate of the other ions. Other constituents may also be present in small amounts. The material may be either amorphous or crystallized ceramic. A particularly preferred composition of the prior art contains 45 weight percent silicon dioxide, 24.5 weight percent sodium oxide, 24.5 weight percent calcium oxide, and 6 weight percent phosphorus pentoxide. This composition is commonly designated as 45S5 (Hench et. al., 1971; Hench and Paschall, 1973; Hench et al. 1977, Hench and Ethridge 1982).

Other controlled surface active ceramics are known to the art including the silicate based biocompatible implant materials disclosed in the following patents:

Broemer et. al. (U.S. Pat. No. 3,981,736 issued Sept. 21, 1976 and U.S. Pat. No. 3,922,155 issued Nov. 25, 1975) disclosed a new biocompatible glass ceramic material containing 20 to 60 weight percent silicon dioxide, 5 to 40 weight percent phosphorus pentoxide, 2.7 to 20 weight percent sodium oxide, 0.4 to 20 weight percent potassium oxide, 2.9 to 30 weight percent magnesium oxide, and 5 to 40 weight percent calcium oxide, and 0.5 to 3.0 weight percent fluorine. This composition (containing magnesium oxide) makes a better glass ceramic because of its crystallization characteristics. They also disclose a crystallization process including times and temperatues of nucleation and crystallization.

Hench and Walker (U.S. Pat. No. 4,171,544 issued Oct. 23, 1979) discloses a new biological material. The material is capable of forming a strong bond with bone due to the high specific surface area developed in a silica rich surface layer on the implant material. Examples of compositions include glasses and glass ceramics with more the 80 weight percent silicon dioxide and inorganic cements such as Portland cement. Calcium, phosphorus, and sodium are not necessary ingredients for the strong bond with bone.

Yagi (U.S. Pat. No. 4,366,253 issued Dec. 28, 1982) disclose another composition and process for producing a glass ceramic with a much lower melting temperature. This composition contains 8 to 48 weight percent (silicon dioxide and germanium dioxide), 8 to 35 weight percent phosphorus pentoxide, 3 to 18 weight percent boron oxide, 16 to 28 weight percent alumium oxide, and 8 to 33 weight percent of (calcium, magnesium, strontium, and barium oxide). The specific times and temperatures of crystallization are disclosed.

Controlled surface active materials are characterized by their ability to form a strong direct chemical bond with living bone in vivo. This type of material has been shown to exhibit a number of changes in vivo. The ceramic's surface activity produces an amorphous gel on the surface into which collagen fibers become embedded. Subsequent heterogeneous hydroxylapatite nucleation and crystallization within the gel proceeds by an ectopic process. This bridges the gap between the bulk glass and the calcium phosphate rich surface. The silicon in this surface gel may be similar in some respects to that which procedes hydroxylapatite mineralization during normal bone growth. Simultaneous to this reaction, hydronium ions are removed from the surrounding fluids by an ion exchange process increasing the local solution pH. The surface pH of 10 developed by glass surface is also similar to the pH (9.4) at which amorphous calcium orthophosphates begin to rapidly precipitate and may be close to the pH present in vivo at regions of high osteoblastic activity. As a result new bone is deposited on the material surface and the material becomes incorporated into the surrounding bone. Implantation of the ceramic into bone defects results in a chemical bond between the ceramic and the bone. This is in significant contrast to single oxide ceramics (silicon dioxide, alumina, magnesium oxide, etc.), metals (stainless steel, Co-Cr alloy), or polymers (acrylic bone cement) which simply fall out of the bone defect during histological preparation or sectioning. No other known nonresorbable material including tricalcium phosphate and hydroxylapatite have consistently shown this type of consistent direct bonding to bone. The overall conclusion is that controlled surface active ceramics play an active role during in vivo ossification.

Other related aspects of the prior art have concentrated on efforts to achieve better attachment of bulk implant devices to bone using two approaches. These include porous coatings on implant devices into which bone is to grow and surface active coatings on the surface of implant devices to which bone attaches.

The prior art reveals several approaches to coatings of biocompatible glass or glass-ceramics onto metallic or ceramic implant bodies, as disclosed in the following patents:

Heimke and Henicke (U.S. Pat. No. 3,919,723 issued Nov. 18, 1975 and U.S. Pat. No. 4,031,571 issued June 28, 1977) disclose a design of a metallic or dense ceramic joint implant and a processes for coating the implant with a bioactive substance such as calcium-aluminum phosphate.

Hench and Greenspan (U.S. Pat. No. 4,103,002 issued July 25, 1978) disclose a process for coating a bioglass onto dense aluminum oxide ceramic implants. The process includes at least two layers of bioglass.

Scharbach et. al. (U.S. Pat. No. 3,987,499 issued Oct. 26, 1976) disclose a metallic hip joint design and a metallic vertebra prosthesis with an enamel coating.

Hench and Buscemi (U.S. Pat. No. 4,234,972 issued Nov. 25, 1980) disclose a process for coating bioglass onto metallic implants. The process allows the coating of a metal with a glass of dissimilar thermal expansion coefficient.

Ogino et. al. (U.S. Pat. No. 4,424,037 issued Jan. 3, 1984) discloses a dental implant design coated with a biologically active glass or glass ceramic coating.

Prior art also reveals several approaches to the use of porous coatings on implants to achieve attachment to bone tissues.

Inukai and Fukuda (U.S. Pat. No. 4,371,484 issued Feb. 1, 1983) disclose a method for producing porous hydroxyapatite.

Tomonaga and Aoki (U.S. Pat. No. 4,222,128 issued Sept. 16, 1980) disclosed a composite material consisting of a mixture of sintered apatite and a polymer resin. The composite is reported to have controlled biocompatibility with bone as well as possessing excellent strength.

Heide et. al. (U.S. Pat. No. 4,309,488 issued Jan. 5, 1982) discloses an implant material consisting of a metallic body with a coating into the surface of resorbable calcium phosphate particles. When the particles dissolve out of the surface in vivo, tissue grows into the pores left behind in the implant.

Draenert (U.S. Pat. No. 4,373,217 issued Feb. 15, 1983) discloses another mixture of ceramic and polymer for use as a prosthetic material. The mixture consists of methacrylate (and/or acrylate) and resorbable tricalcium phosphate. The resorbable ceramic reportedly dissolves permitting tissue to attach to the porous material.

Hench and Walker (U.S. Pat. No. 4,171,544 issued Oct. 23, 1979) disclose a new biological material. The material is capable of forming a strong bond with bone due to the high specific surface area developed in a silica rich surface layer on the implant material. Examples of compositions include glasses and glass ceramics with more than 80 weight percent silicon dioxide and inorganic cements such as Portland cement. Calcium, phosphorus, and sodium are not necessary ingredients for the strong bond with bone.

It is therefore an object of this invention to provide controlled surface active material which may be used to treat and repair general bone resorption and bone damage caused by disease.

It is a second object of this invention to provide controlled surface active ceramic material in granular form wherein the granules are of optimum size and shape to achieve optimum results im treating and repairing general bone resorption and bone damage caused by disease, particularly periodontal disease.

It is another object of this invention to provide a method of treatment of general bone resorption and bone damage adjacent to teeth which is caused by periodontal disease.

It is still another object of this invention to provide a method of restoring a portion of the alveolar ridge in order to provide a anatomical structure upon which traditional dentures may be seated.

It is yet another object of this invention to provide a method of filling defective sockets in alveolar bone after tooth extraction.

SUMMARY OF THE INVENTION

The invention relates to the making of surface active ceramic material in a specific granular form and to a process for the treatment of general bone resorption and disease conditions, in particular to the process combining the utilization of controlled surface active materials of particular size and configuration with a restorative clinical dental surgical technique. The process enables more effective regrowth of natural tissues into the bone defects.

Broadly defined, the method of the present invention comprises the positioning of one or a plurality of compositions of biocompatible tissue stimulating materials in various forms in contact with the bone tissues at sites where it is desirable for a defect to be filled or a bone ridge to be raised. The use of the specific granular material disclosed and claimed in this method enables the appropriate tissues; fibroblasts, odontoblasts, cementoblasts, and osteoblasts to reoccupy the space between and around the granule particles.

The following procedures for forming the synthetic bone graft and utilizing the graft in treating previously irreversible cases of periodontal disease illustrate the new and beneficial application of this synthetic tissue grafting procedure.

DETAILED DESCRIPTION OF THE INVENTION

This invention is a method of repairing periodontal bone loss by filling and packing surface active ceramics into the cavity or void around teeth caused by periodontal shrinkage of the bone and tissue. The surface active ceramics must be a mixture of $SiO_2$, $CaO$, $Na_2O$ and $P_2O_5$ mixed in the correct proportions to be reactive (but not too much so) so as to cause bonding to the bone around the teeth. The surface active ceramics are preferably granular and irregular.

By way of explanation, surface active ceramics have been shown by experiment to be a surface chemically active material which undergoes changes in vivo such that a Ca-P rich surface is formed. Simultaneous to this reaction, $H+$ ions are removed from the surrounding fluids, thus increasing the local tissue pH. As a result, new bone is deposited on the material surface and the ceramic material becomes incorporated into the surrounding bone. No other known material has consistently shown this type of direct bonding to bone.

Figure 1:
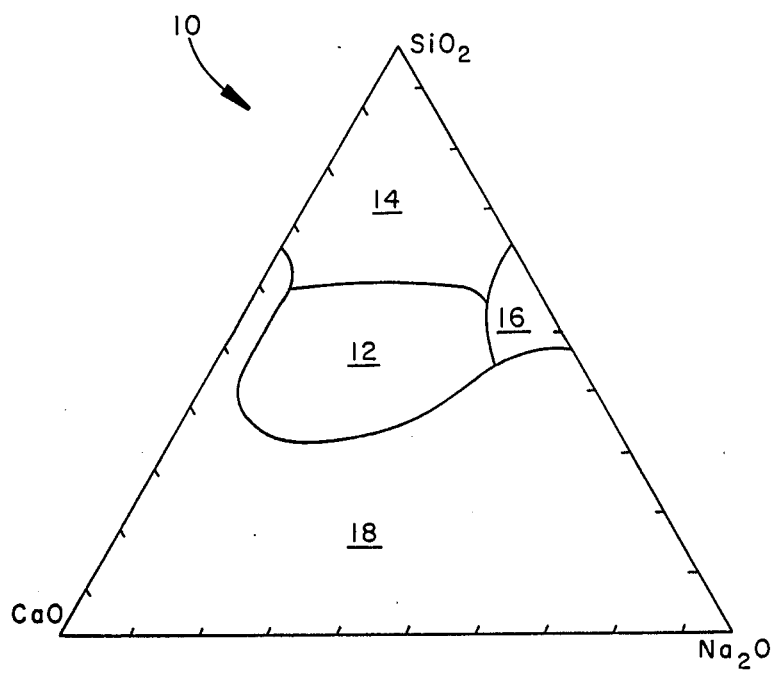
FIG. 1 shows a triaxial composition diagram of controlled surface active ceramics with a constant 6 percent weight of phosphorus pentoxide, wherein the triaxial composition is a mixture of $SiO_2$, $CaO$ and $Na_2O$ with the phosphorus pentoxide.

Looking now at FIG. 1, the triaxial composition diagram is indicated generally by the numeral 10. The diagram illustrates how the compounds $SiO_2$, $CaO$ and $Na_2O$ may be mixed in various proportions to achieve a controlled surface active ceramic having various different characteristics. Although it is not specifically shown on the diagram 10, the diagram 10 also assumes that the surface active ceramic will contain a constant 6 percent by weight of phosphorus pentoxide.

Area 12 on digram 10 shows the ideal compositional range for a controlled surface active ceramic, where bonding to bone occurs after 30 days or less. Area 14 is the compositional range where there is no bonding to bone because the reactivity is too low. Area 16 is the area where there is no bonding to bone because the reactivity is too large. Area 18 is the compositional range where processing is difficult.

The process for making the material for use in treating bone defects such as caused by periodontal disease is as follows. This material as shown in FIG. 1 and described above, is a mixture of $SiO_2$, $CaO$, $Na_2O$ and $P_2O_5$, mixed in the correct proportions to be reactive to the required degree. Appropriate proportions of chemical constituents are weighted and mixed, melted in a high temperature furnace, and cast. To be useful for packing irregular small bone defects as occurs with periodontal bone pockets, the material is processed into a small form for filling irregular shaped defects. One method is to cast the molten material, grind into a granular form, and sieve to an appropriate sieve fraction (pass through one sieve size but remain on a smaller sieve size below the longer sized sieve). The most appropriate sieve range is such as to achieve bone ingrowth between individual grains of the material (0.1 to 1.0 mm). An optimum size for the grains in order to achieve optimum results in repairing bone appears to be grains which are very slightly larger than will pass through U.S. mesh size 60. To remove irregular edges that might cause tissue irritation, the grains are polished with abrasive grains.

An alternative process for fabricating the granular material is to melt the appropriate composition and form into droplets of appropriate size. This is accomplished by spraying a uniform mixture of the appropriate composition into a hot furnace whereupon each grain melts into a spherical molten ball. The molten spheres fall into a lower temperature chamber where they cool into glass spheres. In lieu of spraying the material into a furnace, a droplet generator is used to form uniform size molten spheres. A droplet generator consists of a crucible to contain the molten mixture, an orifice through which the liquid is extruded, and a means for forcing the molten material through the orifice. Molten droplets are formed either by gravitational separation of the droplet from the orifice surface or by Raleigh breakdown of the molten stream ejected from the orifice.

The material may be mixed with one or more of another controlled surface active composition, such as: decalcified or demineralized bone, bone morphogenic protein, or resorbable calcium phosphate mineral compounds. Then it is packaged, sterilized, and otherwise prepared for use as an implant device. The mixing of controlled surface active ceramic with decalcified bone provides a local source for bone proteins to be used during regeneration of bone and periodontal ligament. Mixing with calcium phosphate compounds provides a local source for these elements to be used by the growing bone.

Figure 2:
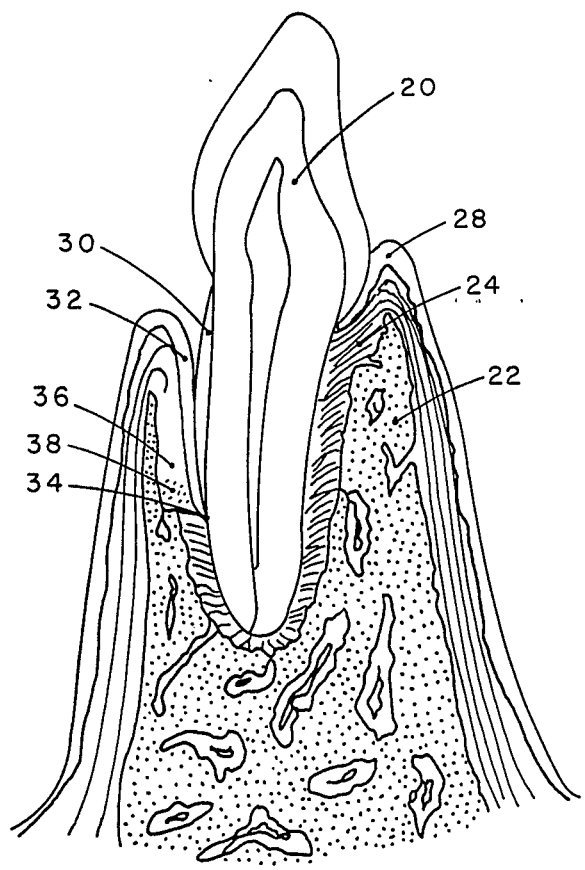
FIG. 2 shows a sectional view of a diseased tooth and socket with a periodontal pocket.

FIG. 2 illustrates a diseased tooth and its socket containing a periodontal pocket. The tooth 20, rests in the alveolar bone 22, being supported by the periodontal ligament 24, and epithelial tissue 28, attaches to the tooth surface isolating the underlying tissues from the oral environment. When plaque 30 builds up on the tooth surface, the epithelial tissue can no longer seal the underlying tissues from the oral environment. This ultimately leads to epithelial downgrowth 32, apical migration of the epithedial attachment 34, and creation of a periodontal bone pocket 36, filled with a fibrous tissue granuloma 38.

The solution to the above-described problem is to restore the natural dental tissues around teeth having bone defects caused by periodontal disease. This is accomplished by the following process for alveolar bone defect site preparation:

Patients receive thorough initial preparation including oral hygiene instructions, scaling, root planing and occulusal equilibration when necessary. Initially a sulcular incision around the involved tooth frees any soft tissue attachment. Modified vertical buccal and lingual incisions to some distance from the implant site aid reflection. This is followed by raising full thickness mucoperisoteal flaps with internally beveled incisions reflected to expose the defect. Epithelialized granulation tissue is removed and bulky gingiva thinned while preserving the vertical dimension of the flap and papilla such that adequate closure is possible. The root surface and the bony defect are then prepared to receive the implant. Since chemicals and endotoxins absorbed into the cementum and the existing granulation tissue might hinder healing, thorough preparation is required to remove them in order to stimulate the healing mechanism. Complete debridement of granulomatous tissue and cementum containing exdotoxins from the exposed cementum is accomplished by thorough root planing. Using sharp curettes the exposed root is scaled and planed until it is hard, smooth, and clean.

The recipient bony pocket site is thoroughly curretted to remove all granulomatous and collagenous tissue over the osseous defect to completely expose the root surface and osseous walls. All transseptal collagen fibers are removed in the process. Exposure of the periodontal ligament provides a source for nourishment and undifferentiated mesenchymal cells. Decortication of the bone lining of the defect with intramarrow penetration is performed since this removes the dense cortical bone barrier permitting better communication between the bony marrow of the alveolar bone and the implant thereby providing a source of mesechymal cells and vascularization of the implant site. Presterilized controlled surface active ceramic implant granules in the form described earlier are inserted and lightly packed into the defect to restore a natural physiologic contour. The site is not overfilled since the implant material will not resorb. The penetration of the patient's own blood will form a coagulum to fill the defect. Once filled with the implant, bleeding also may be induced to cover the site with a clot. The wound is then closed and a periodontal dressing is applied.

Figure 3:
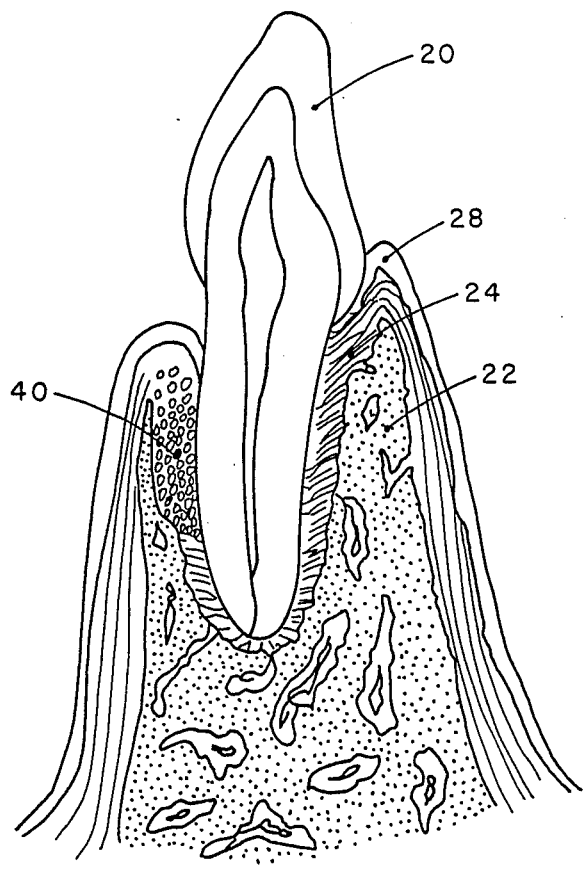
FIG. 3 shows a sectional view of the tooth of FIG. 2 showing a repaired periodontal pocket containing controlled surface active ceramic.

FIG. 3 illustrates a repaired periodontal bone pocket. The bone pocket has been curetted and all fibrous tissue removed and is now filled with controlled surface active ceramic in the granular form described earier.

Figure 4:
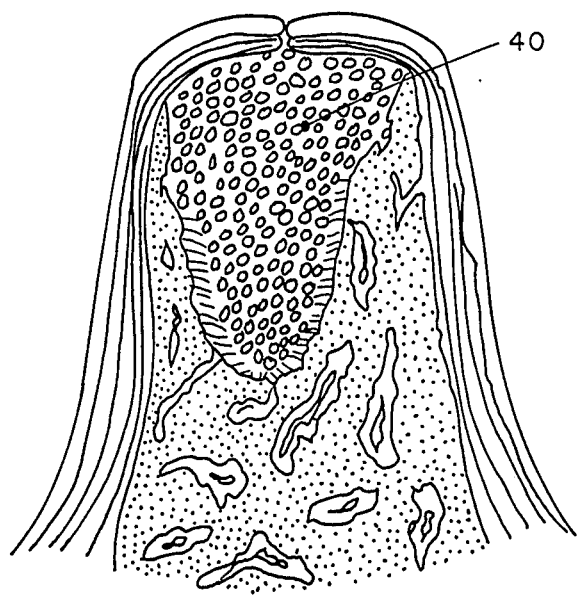
FIG. 4 shows a sectional view of a fresh extraction socket filled with controlled surface active ceramic.

FIG. 4 illustrates a fresh tooth extraction site that has been filled with controlled surface active ceramic 40. The purpose of this process illustrated by FIG. 4 is to fill defects in alveolar bone caused by the extraction of teeth. Filling of the sockets reduces the extent of bone resorption that normally occurs without the impant. After a tooth has been extracted, controlled surface active ceramic in the granular form described earlier is inserted into the fresh socket. The soft tissue surrounding the socket is pulled together and sutured. A periodontal dressing may be applied to help seal the site while it is healing. It is theorized by the inventor that the porous nature of the granular implant is particularly effective in alveolar bone because alveolar bone is characterized by spongy open sites implying a greater need for vascularity than in some other orthopedic implant sites. The open porous nature of the controlled surface active granules permit more vascular tissue to permeate the implant site, thereby establishing a more natural and healty restoration than would be achieved by a single nonporous piece of implant.

Figure 5:
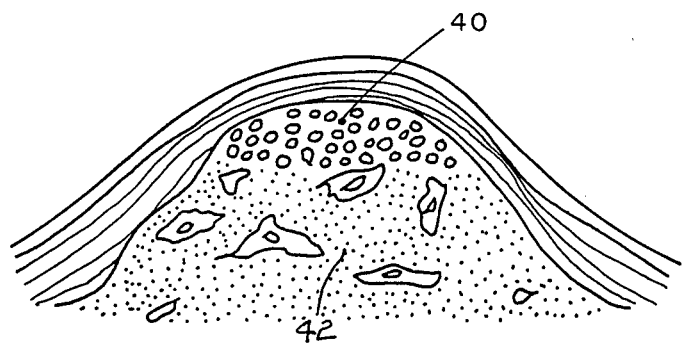
FIG. 5 shows an alveolar bone ridge augmentation using controlled surface active ceramic.

FIG. 5 illustrates an alveolar bone ridge 42, that has been augmented with controlled surface active ceramic 40. The purpose of this process shown in FIG. 5 is to restore a portion of the alveolar ridge in order for traditional dentures to have an anatomical structure upon which the denture is seated. An incision is made in the soft tissue above the aveolar bone that is to be augmented. An instrument is inserted under the tissues and the tissues are separated from the bone. Decortication of the bone may be performed in order to stimulate bone growth. Controlled surface active ceramic in granular form is inserted into the space and the site is surgically closed.

Figure 6:
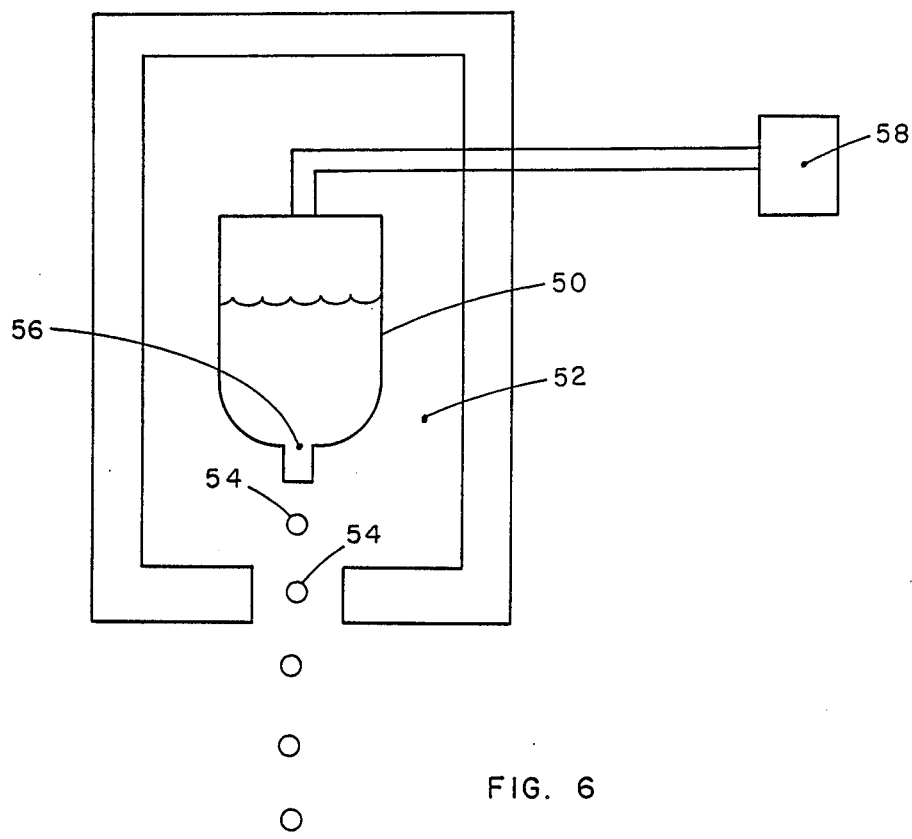
FIG. 6 shows one process for forming precisely sized granules of controlled surface active ceramic.

FIG. 6 illustrates one process for forming precisely sized granules of the surface active ceramic material. The material is melted in a crucible 50, contained in a furnace 52, molten droplets 54, of the material are then caused to extrude out of an orifice in the crucible 56, either by the force exerted by gravity on the melt or by a pneumatic ejection system 58. The molten material solidifies as it falls through air and the solidified particles 60, are collected in a sample holder 62.

It is to be understood that while the detailed drawings and specific examples given, describe the preferred embodiments of the invention they are for the purposes of examples only, that the method of the invention is not limited to the precise details and conditions disclosed and that various changes may be made therein without departing from the spirit of the invention which is defined by the following claims.

What is claimed is:

1. A method of treatment of general bone resorption and bone damage adjacent to teeth, which is caused by periodontal disease comprising:
   making a sulcular incision around one of said diseased teeth to free any soft tissue attachment;
   making modified vertical buccal and lingual incisions to some distance from the implant site:
   raising full thickness mucoperiosteal flaps with internally beveled incisions reflected to expose the defect;
   removing epithelialized granulation tissue;
   thinning bulky gingiva while preserving the vertical dimension of the flap and papilla such that adequate closure is possible;
   preparing the root surface and the bony defect to receive the implant;
   planning of the root in order to accomplish complete debridement of granulomatous tissue and cementum containing exdotoxins from the exposed cementum;
   scaling and planning the exposed root using sharp curettes until the root is hard, smooth and clean;
   curretting the bony socket site to remove all granulomatous and collagenous tissue over the osseous defect, thus exposing the root surface and osseous walls and removing all transseptal collagen fibers;
   performing decortication of the bone lining of the defect with intramarrow penetration, thus removing the dense cortical bone barrier;
   inserting controlled surface active ceramic implant granules into the implant site;
   lightly packing said granules into the defect, to restore a natural physiologic contour without overfilling;
   closing the wound at the implant site; and
   applying a periodontal dressing.

2. The method of treatment of general bone resorption and bone damage adjacent to teeth of claim 1 comprising the preliminary steps of doing scaling, root planning and occulusal equilibration when necessary.

3. The method of treatment of general bone resorption and bone damage adjacent to teeth of claim 1 comprising the step of inducing bleeding to cover the implant site with a clot, after the insertion of the ceramic implant granules into the implant site.

4. A method of regenerative therapy for treating and repairing bone defects comprising:
   preparing a discontinuous mass containing a physiologically compatible and insoluable surface active ceramic; and
   positioning said discontinuous mass adjacent to surgically prepared calcified tissues;
   wherein said surface active ceramic consists of particles having weight proportions in the compositional ranges as follows: silicon dioxide ($SiO_2$), 10 to 60 percent; calcium oxide (CaO) and phosphorus pentoxide ($P_2O_5$), in the ratio of 4:1 to 8:1 comprising 50 to 95 percent; sodium oxide ($Na_2O$), 0 to 25 percent; and potassium oxide ($K_2O$), 0 to 10 percent.

5. A method according to claim 4 for treating and repairing bone defects wherein said discontinuous mass consists of surface active ceramic grains mixed with one or more of demineralized bone, bone morphogenic protein, resorbable calcium phosphate mineral, or collagen.

6. A method according to claim 5 for treating and repairing bone defects comprising mixing a sterile aqueous solution with said ceramic grains.

7. A method according to claim 4 for treating and repairing bone defects comprising delivering said discontinuous mass to the tissues using a syringe.

8. A method according to claim 4 for treating and repairing bone defects wherein 5 to 15 percent of said calcium oxide is replaced by an equal portion of calcium fluoride ($CaF_2$).

9. A method according to claim 4 for treating and repairing bone defects wherein the method for forming said particles comprises:
   casting said molten mixture;
   grinding the resulting casting of said mixture into a mixture having granular form; and
   passing said granular mixture through a sieve device sized and configured to achieve individual grains of the mixture having the range from 0.1 to 1 mm.

10. A method according to claim 4 for treating and repairing bone defects wherein said particles are larger than will pass through U.S. mesh size 60.

11. The method according to claim 10 for treating and repairing bone defects comprising the additional step of polishing said grains with abrasive polishing grains, in order to remove irregular edges from the individual grains of surface active ceramic.

12. The method according to claim 10 for treating and repairing bone defects comprising the additional step of heat treating said grains, in order to remove irregular edges from the individual grains of surface active ceramic.

13. A method according to claim 4 for treating and repairing bone defects wherein the method for casting and forming said particles comprises:
   extruding molten droplets of said mixture from an orifice in said crucible, whereby said droplets solidify as they fall through the air; and
   collecting the solid droplets in a sample holder.

14. The method according to claim 13 for treating and repairing bone defects wherein said extruding is accomplished by allowing the force of gravity to act on the molten ceramic material and cause separation of the droplets from the orifice.

15. The method according to claim 14 for treating and repairing bone defects wherein said extruding is accomplished by the use of a pneumatic ejection system to rapidly extrude a molten stream from the orifice to break down into droplets by the action of surface tension.

16. A method according to claim 4 for treating and repairing bone defects wherein said method more particularly comprises repairing defects in alveolar bone and said process is the filling of sockets in alveolar bone caused by the extraction of teeth comprising:
  insertion of the said discontinuous mass containing physiologically compatible and insoluble surface active ceramic into the fresh socket; and
  surgically closing said tissues.

17. A method of regenerative therapy for treating and repairing bone defects comprising:
  preparing a discontinuous mass containing a physiologically compatible and insoluable surface active ceramic; and
  positioning said discontinuous mass adjacent to surgically prepared calcified tissues;
  wherein said surface active ceramic consists of particles having weight percentages as follows: silicon dioxide ($SiO_2$), 45 percent; calcium oxide (CaO), 24.5 percent; sodium oxide ($Na_2O$), 24.5 percent; and phosphorus pentoxide ($P_2O_5$), 6 percent.

18. A method according to claim 17 for treating and repairing bone defects wherein 5 to 15 percent of calcium oxide is replaced by an equal portion of calcium fluoride ($CaF_2$).

19. A method according to claim 4 for treating and repairing bone defects wherein said defects are defects in alveolar bone; whereby said treatment of alveolar bone defects comprises alveolar ridge augmentation.

20. A method according to claim 19 for treating and repairing bone defects wherein said defects in alveolar bone are repaired by the insertion of the said discontinuous mass containing physiologically compatible and insoluble surface active ceramic into the bone defect comprising:
  making an incision in the soft tissue above the alveolar bone that is to be augmented;
  inserting an instrument under the tissues;
  separating said tissues from said alveolar bone;
  inserting said mass into the available space in the tissues; and
  surgically closing said tissues.

21. A method according to claim 20 for treating and repairing bone defects comprising the step of performing decortication of the bone after the step of separating said tissues from said alveolar bone.

22. A method according to claim 19 for treating and repairing bone defects wherein said available space in the tissues is also adjacent to a dental implant.

23. A method according to claim 17 for treating and repairing bone defects wherein said particles are larger than will pass through U.S. mesh size 60.

24. A method according to claim 17 for treating and repairing bone defects wherein said defects are defects in alveolar bone; whereby said treatment of alveolar bone defects comprises alveolar ridge augmentation.

25. A method according to claim 24 for treating and repairing bone defects wherein said defects in alveolar bone are repaired by the insertion of the said discontinuous mass containing physiologically compatible and insoluble surface active ceramic into the bone defect comprising:
  making an incision in the soft tissue above the alveolar bone that is to be augmented;
  inserting an instrument under the tissues;
  separating said tissues from said alveolar bone;
  inserting said mass into the available space in the tissues; and
  surgically closing said tissues.

26. A method according to claim 24 for treating and repairing bone defects wherein said defects are also adjacent to a dental implant.

27. A method according to claim 17 for treating and repairing bone defects wherein said method more particularly comprises repairing defects in alveolar bone and said process is the filling of sockets in alveolar bone caused by the extraction of teeth comprising:
  insertion of the said discontinuous mass containing physiologically compatible and insoluble surface active ceramic into the fresh socket; and
  surgically closing said tissues.

28. A method of regenerative therapy for treating and repairing bone defects comprising:
  preparing a discontinuous mass containing a physiologically compatible and insoluable surface active ceramic; and
  positioning said discontinuous mass adjacent to surgically prepared calcified tissues;
  wherein said defects are defects in alveolar bone and said method more particularly comprises repairing periodontal pockets adjacent diseased teeth comprising:
  making a sulcular incision around one of said diseased teeth to free any soft tissue attachment;
  making modified vertical buccal and lingual incisions to some distance from the implant site;
  raising full thickness mucoperiosteal flaps with internally beveled incisions reflected to expose the defect;
  removing epithelialized granulation tissue;
  thinning bulky gingiva while preserving the vertical dimension of the flap and papilla such that adequate closure is possible;
  preparing the root surface and the bony defect to receive the implant;
  planning of the root in order to accomplish complete debridement of granulomatous tissue and cementum containing exdotoxins from the exposed cementum;
  scaling and planning the exposed root using sharp curettes until the root is hard, smooth and clean;
  curretting the bony socket site to remove all granulomatous and collagenous tissue over the osseous defect, thus exposing the root surface and osseous walls and removing all transseptal collagen fibers;
  performing decortication of the bone lining of the defect with intramarrow penetration, thus removing the dense cortical bone barrier;
  inserting said discontinuous mass containing said surface active ceramic into the implant site;
  lightly packing said discontinuous mass into the defect, to restore a natural physiologic contour; and
  closing the wound at the implant site.

29. The method according to claim 28 of treating and repairing bone defects comprising the preliminary steps of doing scaling, root planning and occulusal equilibration when necessary.

30. The method according to claim 24 of treating and repairing bone defects comprising the step of inducing bleeding to cover the implant site with a clot, after the insertion of the said discontinuous mass into the implant site.

* * * * *